(12) United States Patent
Seo et al.

(10) Patent No.: US 9,581,729 B2
(45) Date of Patent: Feb. 28, 2017

(54) COMPOUND, PHOTOSENSITIVE RESIN COMPOSITION COMPRISING THE SAME AND COLOR FILTER

(71) Applicant: Samsung SDI Co., Ltd., Yongin-si (KR)

(72) Inventors: Hye-Won Seo, Suwon-si (KR); Eui-Soo Jeong, Suwon-si (KR); Kyu-Young Kim, Suwon-si (KR); Chae-Won Pak, Suwon-si (KR); Myoung-Youp Shin, Suwon-si (KR); Young Lee, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 15/053,004

(22) Filed: Feb. 25, 2016

(65) Prior Publication Data

US 2016/0377764 A1 Dec. 29, 2016

(30) Foreign Application Priority Data

Jun. 23, 2015 (KR) ........................ 10-2015-0089065

(51) Int. Cl.
| | | |
|---|---|---|
| G02B 5/23 | (2006.01) | |
| G02B 1/04 | (2006.01) | |
| G02B 5/22 | (2006.01) | |
| C07F 3/06 | (2006.01) | |
| G02F 1/1335 | (2006.01) | |
| G03F 1/00 | (2012.01) | |
| C09B 67/50 | (2006.01) | |

(52) U.S. Cl.
CPC . G02B 1/04 (2013.01); C07F 3/06 (2013.01); G02B 5/223 (2013.01)

(58) Field of Classification Search
USPC ...... 106/410, 413; 252/586; 349/106; 430/7, 430/270.1, 321
See application file for complete search history.

(56) References Cited

U.S. PATENT DOCUMENTS

| | | | |
|---|---|---|---|
| 5,024,923 A | 6/1991 | Suzuki et al. | |
| 5,346,545 A | 9/1994 | Chassot | |
| 5,998,091 A | 12/1999 | Suzuki | |
| 6,033,813 A | 3/2000 | Endo et al. | |
| 6,733,935 B2 | 5/2004 | Kishimoto et al. | |
| 7,314,511 B2 | 1/2008 | Campbell et al. | |
| 7,517,619 B2 | 4/2009 | Hosaka et al. | |
| 2014/0374677 A1 | 12/2014 | Osada et al. | |

FOREIGN PATENT DOCUMENTS

| | | | |
|---|---|---|---|
| EP | 0337209 A2 | 10/1989 | |
| JP | 02-049785 A | 2/1990 | |
| JP | 06-041458 A | 2/1994 | |
| JP | 07-140654 A | 6/1995 | |
| JP | 10-254133 A | 9/1998 | |
| JP | WO 2012108435 A1 * | 8/2012 | ............ C09B 47/18 |
| JP | 2012-181512 A | 9/2012 | |
| JP | 5277469 A | 5/2013 | |
| JP | 2013-182214 A | 9/2013 | |
| JP | 2013-209623 A | 10/2013 | |
| JP | 2013-213208 A | 10/2013 | |
| JP | 2013-254126 A | 12/2013 | |
| JP | 2014-012814 A | 1/2014 | |
| JP | 2014-028950 A | 2/2014 | |
| JP | 2014-125460 A | 7/2014 | |
| JP | 2015-028602 A | 2/2015 | |
| JP | 2015-072440 A | 4/2015 | |

(Continued)

OTHER PUBLICATIONS

K. A. Volkova, G. V. Avramenkob, V. M. Negrimovskiia, and E. A. Luk'yanetsa, Phthalocyanines and Related Compounds: XLV.1 Nucleophilic Substitution of Chlorine in Tetrachlorophthalonitrile: Synthesis of Aryloxy-Aubstituted Phthalonitriles and Phthalocyanines Derived from Them. Russian Journal of General Chemistry vol. 77 No. 6 2007.*

(Continued)

Primary Examiner — Bijan Ahvazi

(74) Attorney, Agent, or Firm — Additon, Higgins & Pendleton, P.A.

(57) ABSTRACT

A compound represented by Chemical Formula 1, wherein in Chemical Formula 1, each substituent is the same as defined in the detailed description, a photosensitive resin composition including the same, and a color filter manufactured using the photosensitive resin composition are provided.

[Chemical Formula 1]

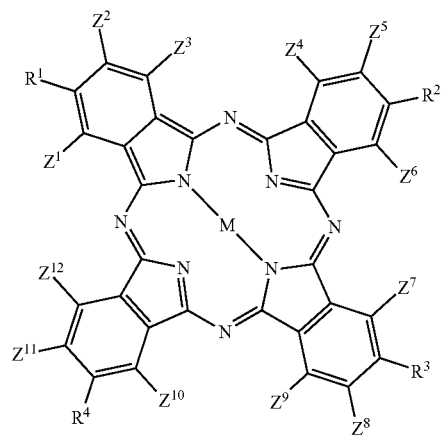

14 Claims, No Drawings

(56) References Cited

FOREIGN PATENT DOCUMENTS

| | | |
|---|---|---|
| KR | 10-1999-0007097 A | 1/1999 |
| KR | 10-2002-0015650 A | 2/2002 |
| KR | 10-2005-0020653 A | 3/2005 |
| KR | 10-2009-0106226 A | 10/2009 |
| KR | 10-2010-0078845 A | 7/2010 |
| KR | 10-2010-0080142 A | 7/2010 |
| KR | 10-2014-0086732 | 7/2014 |

OTHER PUBLICATIONS

Search Report in counterpart Taiwanese Application No. 105106828 dated Jul. 5, 2016, pp. 1.

* cited by examiner

COMPOUND, PHOTOSENSITIVE RESIN COMPOSITION COMPRISING THE SAME AND COLOR FILTER

CROSS-REFERENCE TO RELATED APPLICATION

This application claims priority to and the benefit of Korean Patent Application No. 10-2015-0089065 filed in the Korean Intellectual Property Office on Jun. 23, 2015, the entire disclosure of which is incorporated herein by reference.

FIELD

This disclosure relates to a novel compound, and a photosensitive resin composition and a color filter including the same.

BACKGROUND

A color filter manufactured by using a pigment-type photosensitive resin composition has limits in terms of luminance and contrast ratio caused by pigment particle size. In addition, an imaging sensor device requires a smaller dispersion particle size to form a fine pattern. In order to satisfy the requirement, an attempt to realize a color filter having improved color characteristics such as luminance, contrast ratio and the like has been made by introducing a dye forming no particle instead of a pigment to manufacture a photosensitive resin composition. Accordingly, research on an appropriate compound as the dye used to manufacture the photosensitive resin composition is needed.

SUMMARY

One embodiment provides a novel compound.

Another embodiment provides a photosensitive resin composition including the compound.

Yet another embodiment provides a color filter manufactured using the photosensitive resin composition.

One embodiment of the present invention provides a compound represented by Chemical Formula 1.

[Chemical Formula 1]

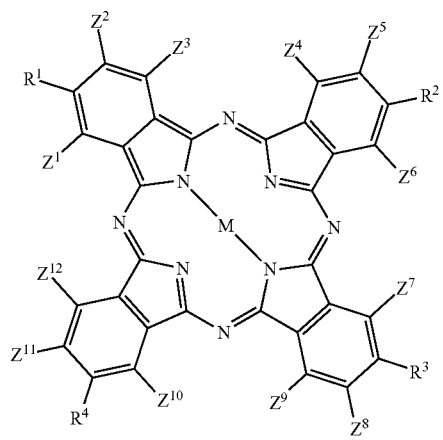

In Chemical Formula 1,

M is Cu, Zn, Co, Al, Ga, In, Ca, Mo, or Mg, $Z^1$ to $Z^{12}$ are the same or different and are each independently Cl or Br, $R^1$ to $R^4$ are the same or different and are each independently a halogen atom, a substituted or unsubstituted C1 to C20 alkyl group, a substituted C3 to C20 alkoxy group, a substituted or unsubstituted C6 to C20 aryl group or a substituted or unsubstituted C6 to C20 aryloxy group, with the proviso that at least one of $R^1$ to $R^4$ is represented by Chemical Formula 2,

[Chemical Formula 2]

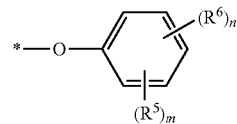

wherein, in Chemical Formula 2, $R^5$ and $R^6$ are the same or different and are each independently an unsubstituted C1 to C10 alkyl group or a C1 to C10 alkyl group-substituted C1 to C10 alkyl group, and m and n are the same or different and are each independently an integer ranging from 0 to 5, provided that 1 m+n 5.

$R^5$ and $R^6$ may each independently include a t-butyl group at the terminal end.

The m and n may be independently an integer of 1.

Chemical Formula 2 may be represented by Chemical Formula 3.

[Chemical Formula 3]

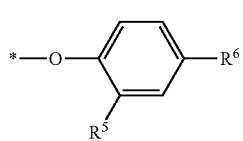

In Chemical Formula 3, $R^5$ and $R^6$ are the same or different and are each independently an unsubstituted C1 to C10 alkyl group or a C1 to C10 alkyl group-substituted C1 to C10 alkyl group.

In exemplary embodiments, at least two of the $R^1$ to $R^4$ may be represented by Chemical Formula 2.

In exemplary embodiments, at least three of the $R^1$ to $R^4$ may be represented by Chemical Formula 2.

In exemplary embodiments, all the $R^1$ to $R^4$ may be represented by Chemical Formula 2.

The compound represented by Chemical Formula 1 may be represented by one or more selected from Chemical Formula 4 to Chemical Formula 11.

[Chemical Formula 4]
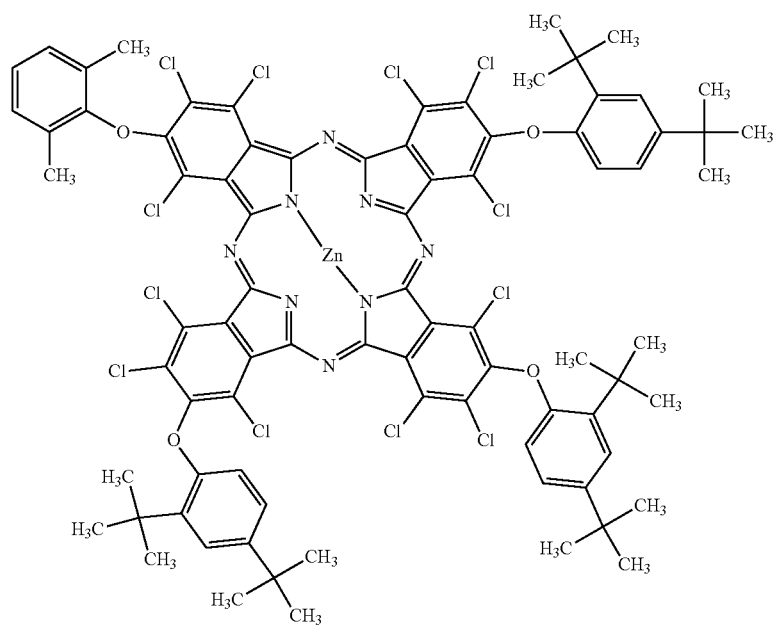
[Chemical Formula 5]
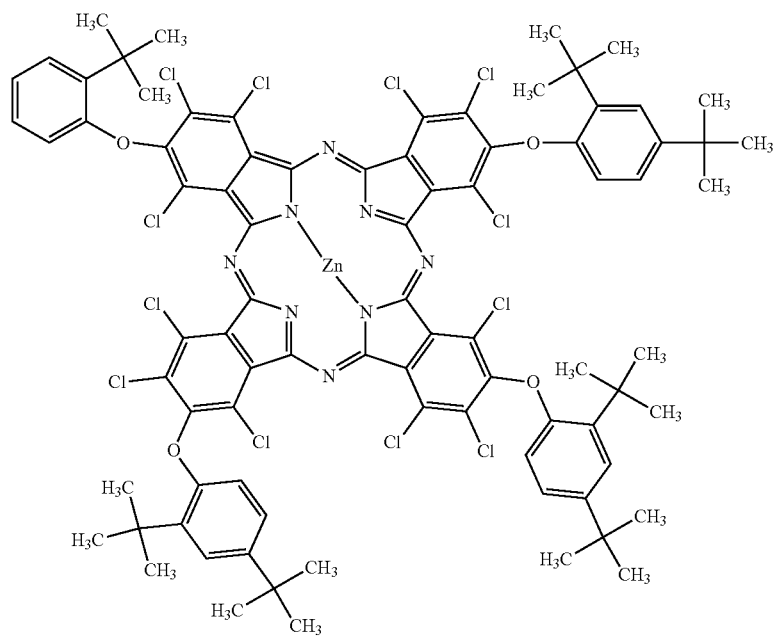

-continued
[Chemical Formula 6]
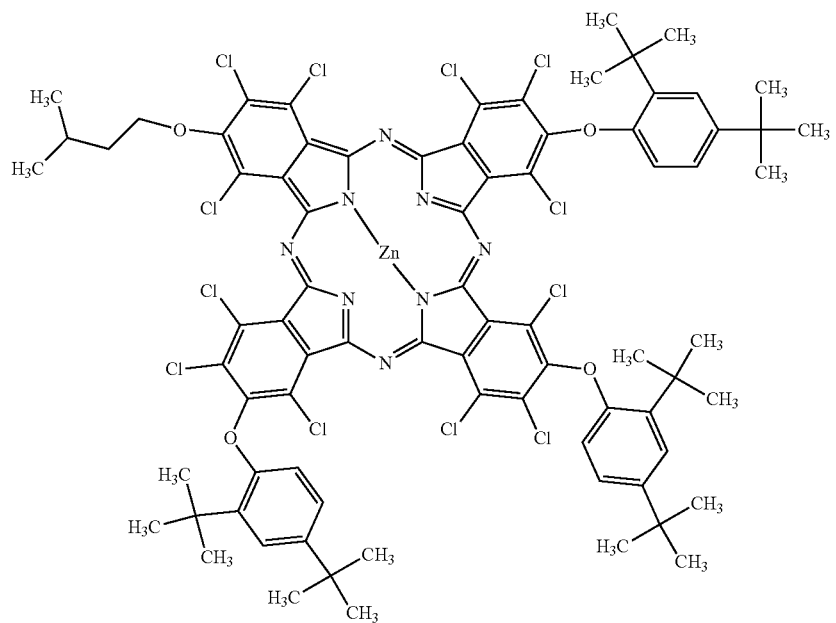
[Chemical Formula 7]
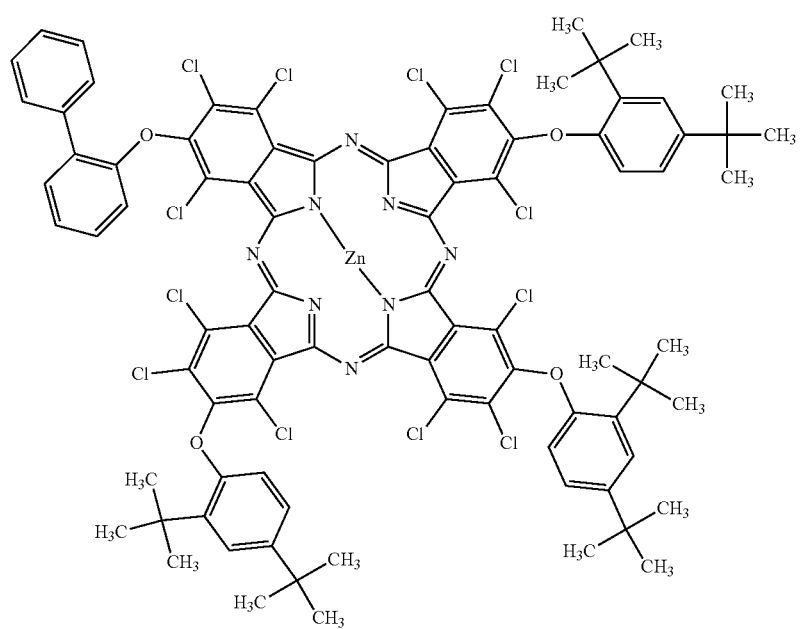

-continued
[Chemical Formula 8]
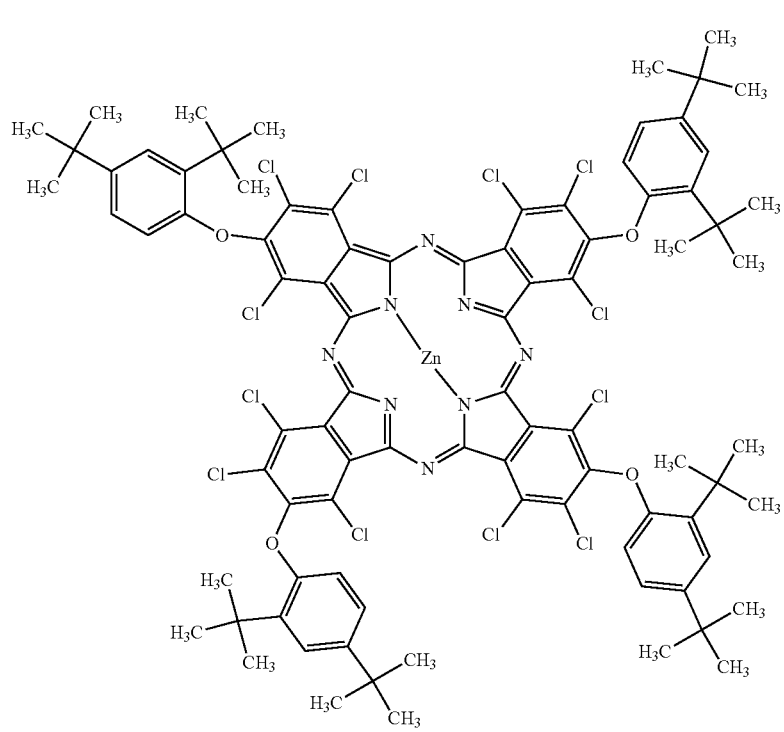
[Chemical Formula 9]
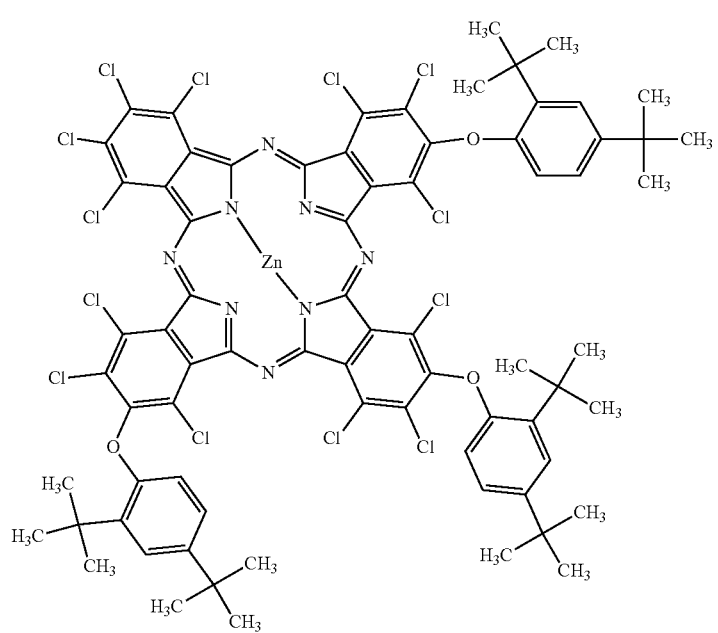

-continued

[Chemical Formula 10]

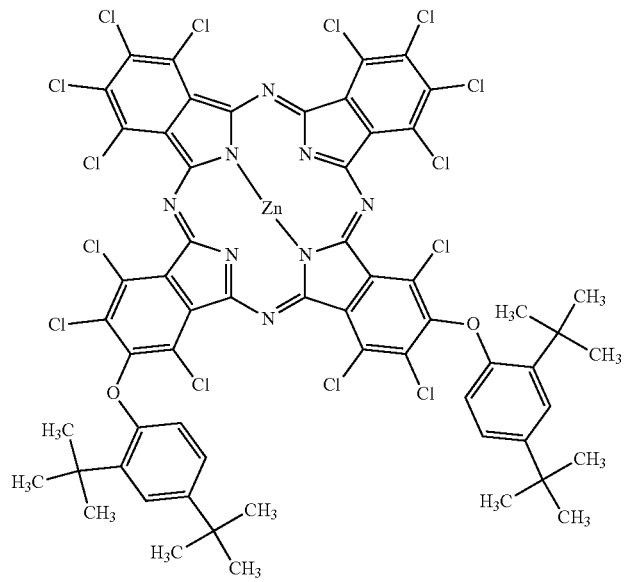

[Chemical Formula 11]

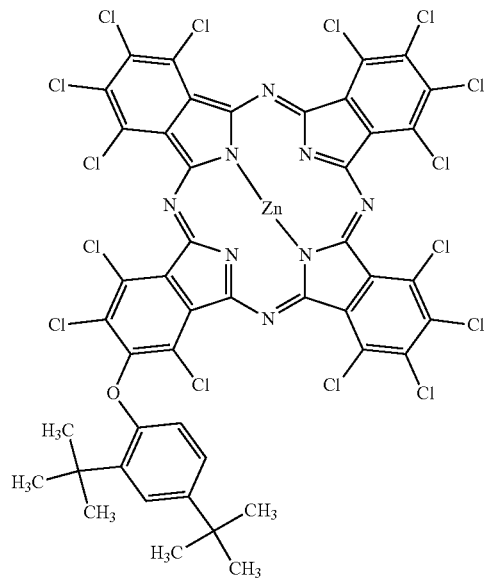

The compound may be a green dye.

The green dye may have a maximum transmittance in a wavelength of about 445 nm to about 560 nm.

Another embodiment provides a photosensitive resin composition including the compound.

The photosensitive resin composition may further include an alkali soluble resin, a photopolymerizable compound, a photopolymerization initiator, and a solvent.

The photosensitive resin composition may further include a pigment.

The pigment may be a yellow pigment.

Another embodiment provides a color filter manufactured using the photosensitive resin composition.

Other embodiments of the present invention are included in the following detailed description.

The compound according to one embodiment can have excellent green spectral characteristics, a high molar extinction coefficient, and improved solubility for an organic solvent and thus, may be used as a dye during preparation of a photosensitive resin composition for a green color filter, and a color filter including the dye may have excellent luminance and contrast ratio.

DETAILED DESCRIPTION

The present invention will be described more fully hereinafter with reference to the accompanying drawings, in which exemplary embodiments of the present invention are shown. This invention may, however, be embodied in many different forms and should not be construed as limited to the exemplary embodiments set forth herein. These exemplary embodiments disclosed in this specification are provided so that this disclosure will satisfy applicable legal requirements.

As used herein, when a specific definition is not otherwise provided, the term "substituted" refers to one substituted with a substituent selected from a halogen (F, Br, Cl, or I), a hydroxy group, a nitro group, a cyano group, a thiol group, an amino group ($NH_2$, $NH(R^{200})$ or $N(R^{201})(R^{202})$, wherein $R^{200}$, $R^{201}$ and $R^{202}$ are the same or different and are each independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group and/or a substituted or unsubstituted heterocyclic group, instead of at least one of a functional group and/or hydrogen.

As used herein, when a specific definition is not otherwise provided, the term "alkyl group" refers to a C1 to C20 alkyl group, for example a C1 to C15 alkyl group, the term "cycloalkyl group" refers to a C3 to C20 cycloalkyl group, for example a C3 to C18 cycloalkyl group, the term "alkoxy group" refers to a C1 to C20 alkoxy group, for example a C1 to C18 alkoxy group, the term "aryl group" refers to a C6 to C20 aryl group, for example a C6 to C18 aryl group, the term "alkenyl group" refers to a C2 to C20 alkenyl group, for example a C2 to C18 alkenyl group, the term "alkylene group" refers to a C1 to C20 alkylene group, for example C1 to C18 alkylene group, and the term "arylene group" refers to a C6 to C20 arylene group, for example a C6 to C16 arylene group.

As used herein, when a specific definition is not otherwise provided, the term "alicyclic organic group" refers to a C3 to C30 cycloalkyl group, a C3 to C30 cycloalkenyl group, a C3 to C30 cycloalkynyl group, a C3 to C30 cycloalkylene group, a C3 to C30 cycloalkenylene group, or a C3 to C30 cycloalkynylene group, for example a C3 to C20 cycloalkyl group, a C3 to C20 cycloalkenyl group, a C3 to C20 cycloalkynyl group, a C3 to C20 cycloalkylene group, a C3 to C20 cycloalkenylene group, or a C3 to C20 cycloalkynylene group; and the term "heterocyclic group" refers to a C2 to C30 heterocycloalkyl group, a C2 to C30 heterocycloalkenyl group, a C2 to C30 heterocycloalkynyl group, a C2 to C30 heterocycloalkylene group, a C2 to C30 heterocycloalkenylene group, or a C2 to C30 heterocycloalkynylene group, for example a C2 to C20 heterocycloalkyl group, a C2 to C20 heterocycloalkenyl group, a C2 to C20 heterocycloalkynyl group, a C2 to C20 heterocycloalkylene group, a C2 to C20 heterocycloalkenylene group, or a C2 to C20 heterocycloalkynylene group.

As used herein, when a specific definition is not otherwise provided, the term "hetero" refers to at least one heteroatom such as N, O, S and/or P in a chemical formula.

As used herein, when a specific definition is not otherwise provided, "(meth)acrylate" refers to "acrylate" and/or "methacrylate" and "(meth)acrylic acid" refers to "acrylic acid" and/or "methacrylic acid."

As used herein, when a definition is not otherwise provided, the term "combination" refers to mixing or copolymerization. In addition, the term "copolymerization" refers to block copolymerization and/or random copolymerization, and "copolymer" refers to a block copolymer and/or a random copolymer.

In the chemical formula of the present specification, unless a specific definition is otherwise provided, hydrogen is bonded at the position when a chemical bond is not drawn where a bond would otherwise appear.

As used herein, when a specific definition is not otherwise provided, "*" indicates a point where the same or different atom or chemical formula is linked.

One embodiment provides a compound represented by Chemical Formula 1.

[Chemical Formula 1]

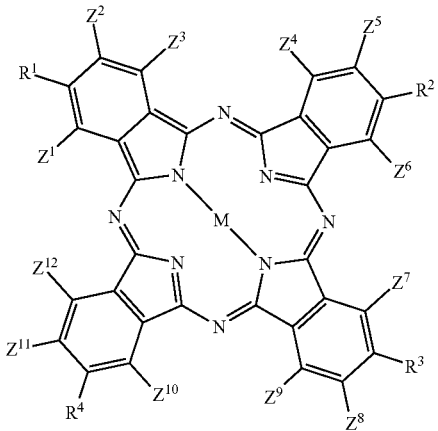

In Chemical Formula 1,
M is Cu, Zn, Co, Al, Ga, In, Ca, Mo, or Mg,
$Z^1$ to $Z^{12}$ are the same or different and are each independently Cl or Br,
$R^1$ to $R^4$ are the same or different and are each independently a halogen atom, a substituted or unsubstituted C1 to C20 alkyl group, a substituted C3 to C20 alkoxy group, a substituted or unsubstituted C6 to C20 aryl group or a substituted or unsubstituted C6 to C20 aryloxy group, with the proviso that at least one of $R^1$ to $R^4$ is represented by Chemical Formula 2,

[Chemical Formula 2]

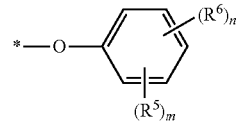

wherein, in Chemical Formula 2,
$R^5$ and $R^6$ are the same or different and are each independently an unsubstituted C1 to C10 alkyl group or a C1 to C10 alkyl group-substituted C1 to C10 alkyl group, and
m and n are the same or different and are independently an integer ranging from 0 to 5, provided that $1 \le m+n \le 5$.

The compound represented by Chemical Formula 1 according to one embodiment can have excellent green spectral characteristics and high luminance. Furthermore, the compound represented by Chemical Formula 1 includes an aryloxy group represented by Chemical Formula 2, the aryloxy group includes an alkyl group as a substituent, and the alkyl group is either non-substituted or substituted itself, and accordingly, the compound may have improved solubility in an organic solvent.

In an exemplary embodiment, M may be Zn.

In exemplary embodiments, $R^5$ and $R^6$ may each independently be a substituent including an isopropyl group or a t-butyl group, for example a t-butyl group at the terminal end. When the alkyl group, which is a substituent for the aryloxy group represented by Chemical Formula 2, includes an isopropyl group or a t-butyl group, for example, a t-butyl group at the terminal end, this can increase solubility in an organic solvent and provide excellent luminance.

The m and n may be independently an integer of 1.

The aryloxy group represented by Chemical Formula 2 includes two alkyl groups that are substituted or unsubstituted with an alkyl group as a substituent and may have improved solubility in an organic solvent compared with one including one alkyl group as a substituent.

For example, Chemical Formula 2 may be represented by Chemical Formula 3.

[Chemical Formula 3]

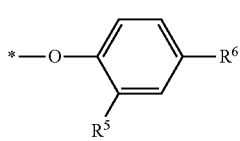

In Chemical Formula 3, $R^5$ and $R^6$ are the same or different and are each independently an unsubstituted C1 to C10 alkyl group or a C1 to C10 alkyl group-substituted C1 to C10 alkyl group.

$R^5$ can be present at an ortho position with respect to the oxygen atom of the aryloxy group, and $R^6$ may be present at a para position with respect to the oxygen atom of the the aryloxy group. When the alkyl substituent is present at the ortho position and the para position with respect to the oxygen atom of the the aryloxy group, improved solubility and luminance can be obtained, as compared with when the alkyl substituent is present at other positions.

In exemplary embodiments, at least two of $R^1$ to $R^4$, for example, at least three of $R^1$ to $R^4$, may be represented by Chemical Formula 2. For example, all of $R^1$ to $R^4$ may be represented by Chemical Formula 2.

As increasing numbers of a substituent represented by Chemical Formula 2 is present, improved solubility of the compound according to one embodiment in an organic solvent may be obtained.

The compound represented by Chemical Formula 1 may be represented by one or more selected from compounds represented by Chemical Formula 4 to Chemical Formula 11.

[Chemical Formula 4]

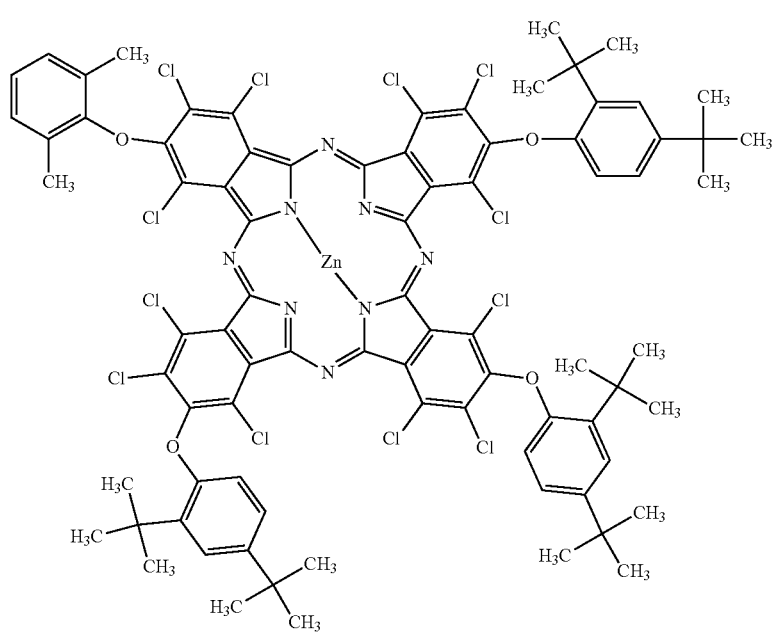

[Chemical Formula 5]

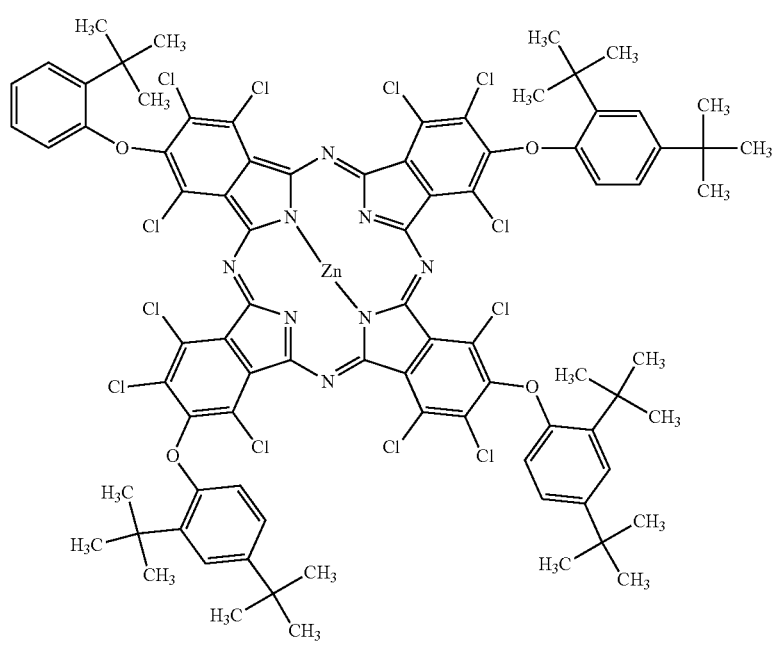

[Chemical Formula 6]
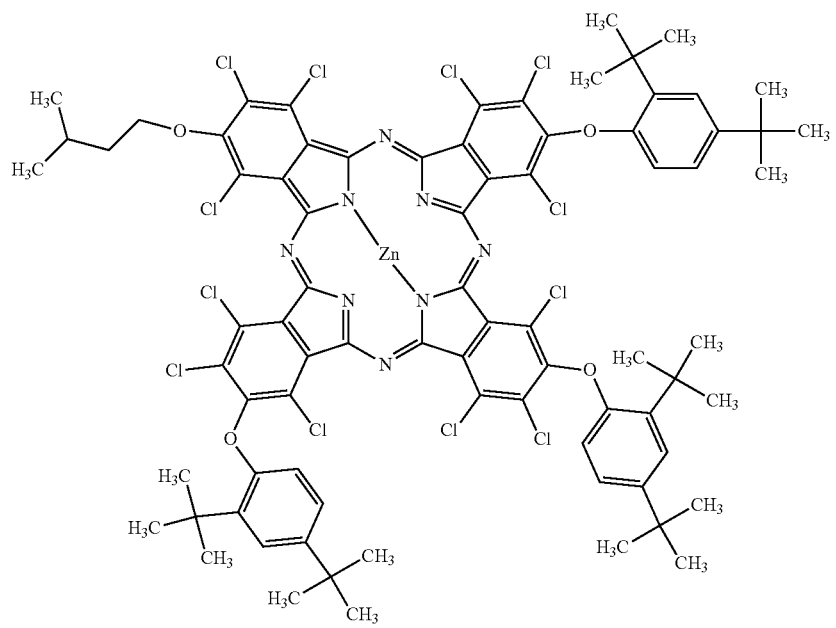
[Chemical Formula 7]
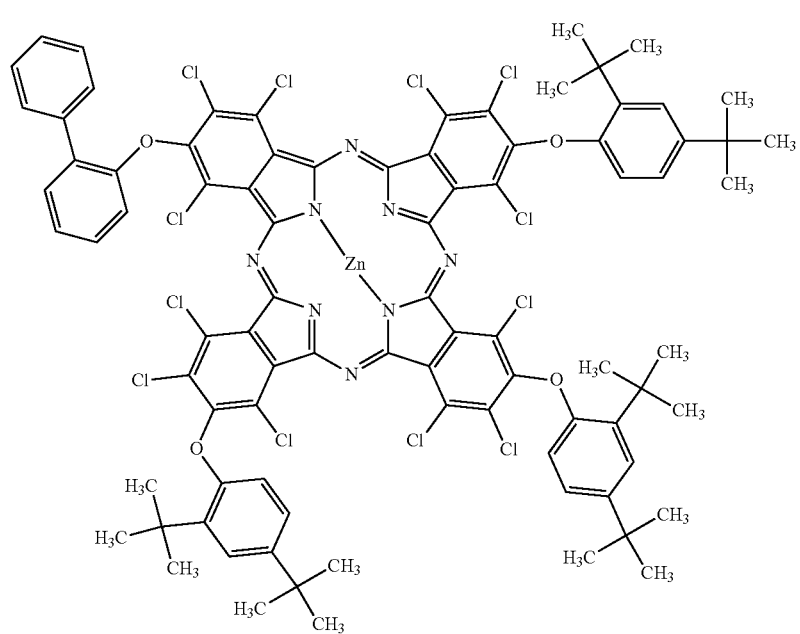

-continued
[Chemical Formula 8]
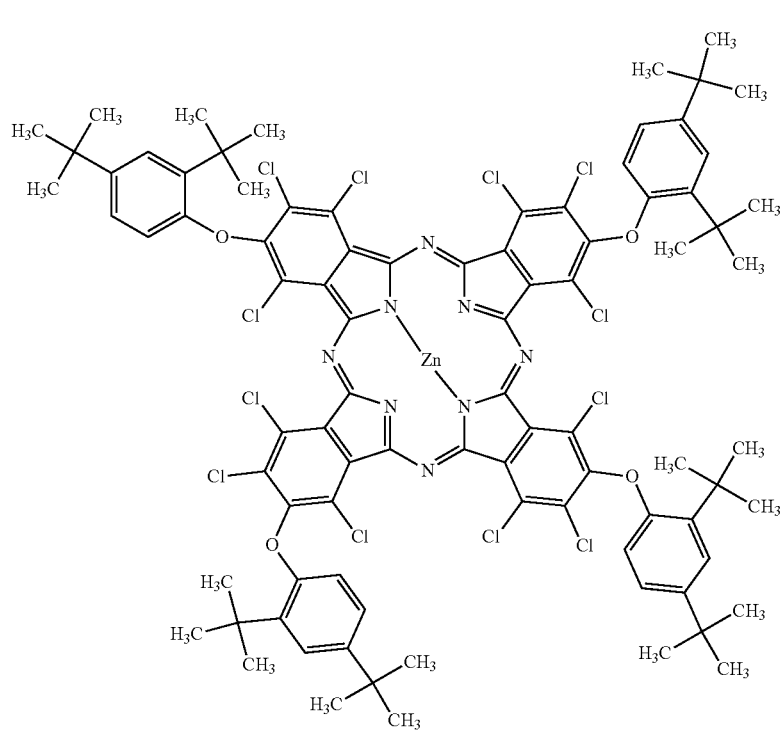
[Chemical Formula 9]
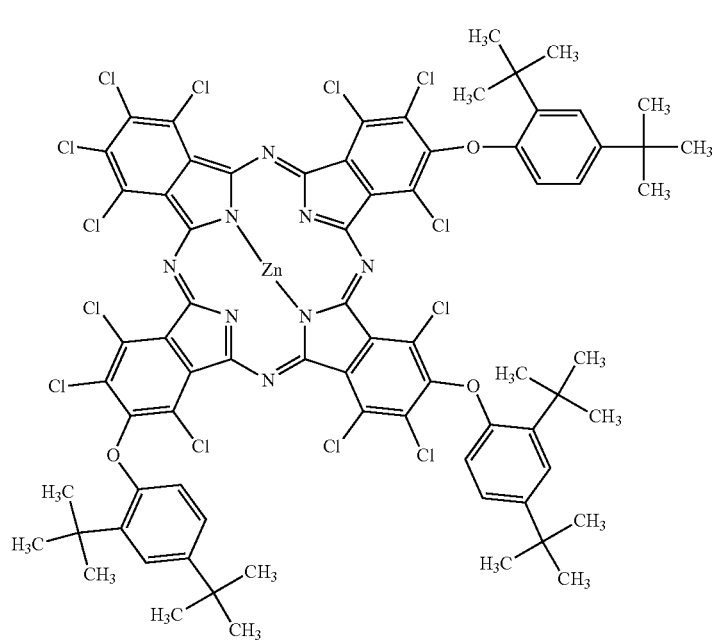

-continued

[Chemical Formula 10]

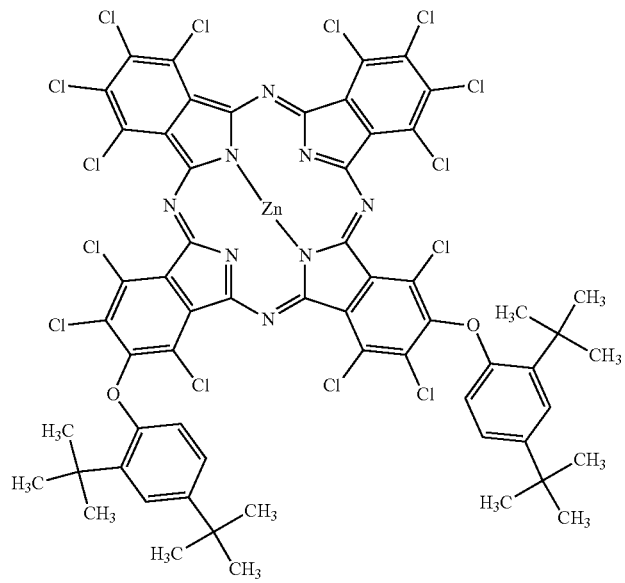

[Chemical Formula 11]

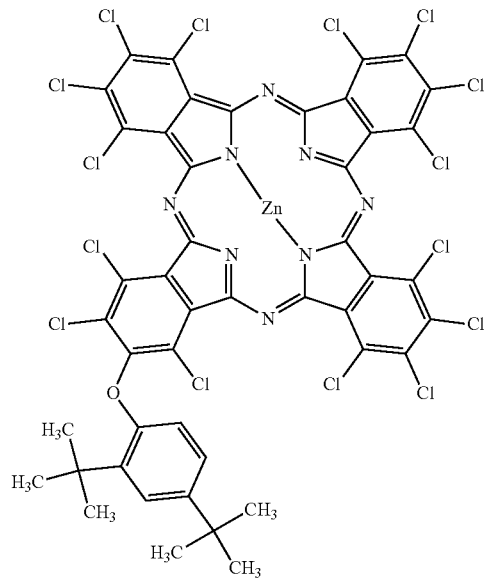

Since the compound according to one embodiment (a compound of Chemical Formula 1) may realize a clearer color even when used in a smaller amount due to the substituted alkyl group, a display device having excellent color characteristics such as luminance, a contrast ratio and the like may be manufactured by using the compound as a colorant. For example, the compound may be a colorant, for example a dye, for example a green dye, which may have for example maximum transmittance in a wavelength of about 445 nm to about 560 nm.

In general, a dye is the most expensive of the components used in a color filter. Large amounts of the expensive dye may need to be used to accomplish a desired effect, for example, high luminance, a high contrast ratio or the like, which can increase the unit cost of production. However, when the compound according to one embodiment (a compound of Chemical Formula 1) is used as a dye in a color filter, the compound may accomplish excellent color characteristics such as high luminance, a high contrast ratio and the like even when used in a small amount and thus can reduce the unit cost of production.

Furthermore, when the compound according to one embodiment (a compound of Chemical Formula 1) includes a substituent represented by Chemical Formula 3, solubility in an organic solvent and luminance can be even further improved.

According to one embodiment, a photosensitive resin composition including the compound according to the above embodiment (a compound of Chemical Formula 1) is provided.

In embodiments, the photosensitive resin composition can include the compound according to the above embodiment, an alkali soluble resin, a photopolymerizable compound, a photopolymerization initiator, and a solvent. The photosensitive resin composition may further include a pigment.

The compound according to one embodiment (a compound of Chemical Formula 1) plays a role of a colorant, for example, a dye, for example, a green dye, in the photosensitive resin composition and may realize excellent color characteristics.

The photosensitive resin composition may include the compound according to one embodiment (a compound of Chemical Formula 1) in an amount of about 1 wt % to about 10 wt %, for example, about 3 wt % to about 7 wt %, based on the total amount (total weight, 100 wt %) of the photosensitive resin composition. In some embodiments, the photosensitive resin composition may include the compound of Chemical Formula 1 in an amount of about 1, 2, 3, 4, 5, 6, 7, 8, 9, or 10 wt %. Further, according to some embodiments, the amount of the compound of Chemical Formula 1 can be in a range from about any of the foregoing amounts to about any other of the foregoing amounts.

When the compound according to one embodiment is included in an amount within the above range, color reproducibility and contrast ratio can be excellent.

The photosensitive resin composition may further include a pigment, for example, a yellow pigment.

Examples of the yellow pigment may include without limitation C.I. pigment yellow 139, C.I. pigment yellow 138, C.I. pigment yellow 150, and the like in a color index, and these pigments may be used singularly or as a mixture of two or more.

The pigment may be included in a form of pigment dispersion in the photosensitive resin composition.

The pigment dispersion may include a solid pigment, a solvent, and a dispersing agent for uniformly dispersing the pigment into the solvent.

The pigment dispersion may include solid pigment in an amount of about 1 wt % to about 20 wt %, for example, about 8 wt % to about 20 wt %, for example, about 8 wt % to about 15 wt %, for example, about 10 wt % to about 20 wt %, for example, about 10 wt % to about 15 wt %, based on the total amount (total weight, 100 wt %) of the pigment dispersion.

The dispersing agent may be a non-ionic dispersing agent, an anionic dispersing agent, and/or a cationic dispersing agent, and the like. Examples of the dispersing agent may include without limitation polyalkylene glycols and esters thereof, polyoxyalkylenes, polyhydric alcohol ester alkylene oxide addition products, alcohol alkylene oxide addition products, sulfonate esters, sulfonate salts, carboxylate esters, carboxylate salts, alkylamide alkylene oxide addition products, alkyl amines, and the like, and may be used singularly or as a mixture of two or more.

Commercially available examples of the dispersing agent may include without limitation DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; and/or PB711, PB821, and the like made by Ajinomoto Inc.

The pigment dispersion may include the dispersing agent in an amount of about 1 wt % to about 20 wt % based on the total amount (total weight, 100 wt %) of the pigment dispersion. When the dispersing agent is included in an amount within the above range, dispersion in the photosensitive resin composition may be improved due to an appropriate viscosity, and thus optical, physicochemical quality of an article may be maintained.

Examples of the solvent for the pigment dispersion may include without limitation ethylene glycol acetate, ethylcellosolve, propylene glycol methyletheracetate, ethyllactate, polyethylene glycol, cyclohexanone, propylene glycol methylether, and the like, and mixtures thereof.

When present, the photosensitive resin composition may include the pigment dispersion in an amount of about 10 wt % to about 20 wt %, for example, about 12 wt % to about 18 wt %, based on the total amount (total weight, 100 wt %) of the photosensitive resin composition. In some embodiments, the photosensitive resin composition may include the pigment dispersion in an amount of about 10, 11, 12, 13, 14, 15, 16, 17, 18, 19, or 20 wt %. Further, according to some embodiments, the amount of the pigment dispersion can be in a range from about any of the foregoing amounts to about any other of the foregoing amounts.

When the pigment dispersion is included in an amount within the above range, a process margin can be advantageously secured, and color reproducibility and contrast ratio can be excellent.

The alkali soluble resin may be an acrylic-based resin.

The acrylic-based resin is a copolymer of a first ethylenic unsaturated monomer and a second ethylenic unsaturated monomer that is copolymerizable therewith, and is a resin including at least one acrylic-based repeating unit.

The first ethylenic unsaturated monomer is an ethylenic unsaturated monomer including at least one carboxyl group. Examples of the first ethylenic unsaturated monomer include without limitation (meth)acrylic acid, maleic acid, itaconic acid, fumaric acid, and the like, and combinations thereof.

The acrylic-based resin may include the first ethylenic unsaturated monomer in an amount of about 5 to about 50 wt %, for example about 10 to about 40 wt %, based on the total amount (total weight, 100 wt %) of the acrylic-based resin.

Examples of the second ethylenic unsaturated monomer may include without limitation aromatic vinyl compounds such as styrene, α-methylstyrene, vinyl toluene, vinylbenzylmethylether and the like; unsaturated carboxylate ester compounds such as methyl(meth)acrylate, ethyl(meth)acrylate, butyl(meth)acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; unsaturated carboxylic acid amino alkyl ester compounds such as 2-aminoethyl(meth)acrylate, 2-dimethylaminoethyl(meth)acrylate, and the like; carboxylic acid vinyl ester compounds such as vinyl acetate, vinyl benzoate, and the like; unsaturated carboxylic acid glycidyl ester compounds such as glycidyl(meth)acrylate, and the like; vinyl cyanide compounds such as (meth)acrylonitrile and the like; unsaturated amide compounds such as (meth)acrylamide, and the like; and the like, and may be used singularly or as a mixture of two or more.

Examples of the acrylic-based resin may include without limitation an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like. These may be used singularly or as a mixture of two or more.

The alkali soluble resin may have a weight average molecular weight of about 3,000 g/mol to about 150,000 g/mol, for example about 5,000 g/mol to about 50,000 g/mol, and as another example about 20,000 g/mol to about 30,000 g/mol. When the acrylic-based resin has a weight average molecular weight within the above range, the photosensitive resin composition can have good physical and chemical properties, appropriate viscosity, and close contacting (adhesive) properties with a substrate during manufacture of a color filter.

The acrylic-based resin may have an acid value of about 15 mgKOH/g to about 60 mgKOH/g, for example about 20 mgKOH/g to about 50 mgKOH/g. When the acrylic-based resin has an acid value within the above range, a pixel pattern may have excellent resolution.

The photosensitive resin composition can include the alkali soluble resin in an amount of about 1 wt % to about 30 wt %, for example about 1 wt % to about 20 wt %, based on the total amount (total weight, 100 wt %) of the photosensitive resin composition. In some embodiments, the photosensitive resin composition may include the alkali soluble resin in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. Further, according to some embodiments, the amount of the alkali soluble resin can be in a range from about any of the foregoing amounts to about any other of the foregoing amounts.

When the alkali soluble resin is included in an amount within the above range, developability may be improved and excellent surface smoothness may be improved due to improved cross-linking during the manufacture of a color filter.

The photopolymerizable compound may be mono-functional and/or multi-functional ester of (meth)acrylic acid including at least one ethylenic unsaturated double bond.

The photopolymerizable compound has the ethylenic unsaturated double bond and thus, may cause sufficient polymerization during exposure in a pattern-forming process and form a pattern having excellent heat resistance, light resistance, and chemical resistance.

Examples of the photopolymerizable compound may include without limitation ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolac epoxy (meth)acrylate, and the like, and combinations thereof.

Commercially available examples of the photopolymerizable compound include without limitation the following. Examples of a mono-functional ester of (meth)acrylic acid may include without limitation Aronix M-101®, M-111®, and/or M-114® (Toagosei Chemistry Industry Co., Ltd.); KAYARAD TC-110S® and/or TC-120S® (Nippon Kayaku Co., Ltd.); V-158® and/or V-2311® (Osaka Organic Chemical Ind., Ltd.), and the like. Examples of a difunctional ester of (meth)acrylic acid may include without limitation Aronix M-210®, M-240®, and/or M-6200® (Toagosei Chemistry Industry Co., Ltd.), KAYARAD HDDA®, HX-220®, and/or R-604® (Nippon Kayaku Co., Ltd.), V-260®, V-312®, and/or V-335 HP® (Osaka Organic Chemical Ind., Ltd.), and the like. Examples of a tri-functional ester of (meth)acrylic acid may include without limitation Aronix M-309®, M-400®, M-405®, M-450®, M-7100®, M-8030®, and/or M-8060® (Toagosei Chemistry Industry Co., Ltd.), KAYARAD TMPTA®, DPCA-20®, DPCA-30®, DPCA-60®, and/or DPCA-120® (Nippon Kayaku Co., Ltd.), V-295®, V-300®, V-360®, V-GPT®, V-3PA®, and/or V-400® (Osaka Yuki Kayaku Kogyo Co. Ltd.), and the like. These may be used singularly or as a mixture of two or more.

The photopolymerizable compound may be treated with acid anhydride to improve developability.

The photosensitive resin composition may include the photopolymerizable compound in an amount of about 1 wt % to about 15 wt %, for example about 5 wt % to about 10 wt %, based on the total amount (total weight, 100 wt %) of the photosensitive resin composition. In some embodiments, the photosensitive resin composition may include the photopolymerizable compound in an amount of about 1, 2, 3, 4, 5, 6, 7, 8, 9, 10, 11, 12, 13, 14, or 15 wt %. Further, according to some embodiments, the amount of the photopolymerizable compound can be in a range from about any of the foregoing amounts to about any other of the foregoing amounts.

When the photopolymerizable compound is included in an amount within the above range, the photopolymerizable compound can be sufficiently cured during exposure in a pattern-forming process and can have excellent reliability, and developability for alkali developing solution may be improved.

The photopolymerization initiator can be a generally-used initiator for a photosensitive resin composition, for example an acetophenone-based compound, a benzophenone-based compound, a thioxanthone-based compound, a benzoin-based compound, a triazine-based compound, an oxime-based compound, or a combination thereof.

Examples of the acetophenone-based compound may include without limitation 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like, and combinations thereof.

Examples of the benzophenone-based compound may include without limitation benzophenone, benzoyl benzoate, benzoyl methyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like, and combinations thereof.

Examples of the thioxanthone-based compound may include without limitation thioxanthone, 2-methylthioxanthone, isopropyl thioxanthone, 2,4-diethyl thioxanthone, 2,4-diisopropyl thioxanthone, 2-chlorothioxanthone, and the like, and combinations thereof.

Examples of the benzoin-based compound may include without limitation benzoin, benzoin methyl ether, benzoin ethyl ether, benzoin isopropyl ether, benzoin isobutyl ether, benzyldimethyl ketal, and the like, and combinations thereof.

Examples of the triazine-based compound may include without limitation 2,4,6-trichloro-s-triazine, 2-phenyl-4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like, and combinations thereof.

Examples of the oxime-based compound may include without limitation O-acyloxime-based compounds, 2-(o-benzoyloxime)-1-[4-(phenylthio)phenyl]-1,2-octandione, 1-(o-acetyloxime)-1-[9-ethyl-6-(2-methylbenzoyl)-9H-carbazol-3-yl]ethanone, O-ethoxycarbonyl-α-oxyamino-1-phenylpropan-1-one and the like, and combinations thereof. Examples of the O-acyloxime-based compound may include without limitation 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione2-oxime-O-benzoate, 1-(4-phenylsulfanyl phenyl)-octan-1-one oxime-O-acetate and 1-(4-phenylsulfanyl phenyl)-butan-1-oneoxime-O-acetate, and the like, and combinations thereof.

The photopolymerization initiator may further include without limitation one or more of a carbazole-based compound, a diketone-based compound, a sulfonium borate-based compound, a diazo-based compound, an imidazole-based compound, a biimidazole-based compound, and the like, in addition to or instead of the above compounds.

The photopolymerization initiator may be used with a photosensitizer capable of causing a chemical reaction by absorbing light and becoming excited and then, transferring its energy.

Examples of the photosensitizer may include without limitation tetraethylene glycol bis-3-mercapto propionate, pentaerythritol tetrakis-3-mercapto propionate, dipentaerythritol tetrakis-3-mercapto propionate, and the like, and combinations thereof.

The photosensitive resin composition may include the photopolymerization initiator in an amount of about 0.01 wt % to about 10 wt %, for example about 0.1 wt % to about 5 wt %, based on the total amount (total weight, 100 wt %) of the photosensitive resin composition. In some embodiments, the photosensitive resin composition may include the photopolymerization initiator in an amount of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt %. Further, according to some embodiments, the amount of the photopolymerization initiator can be in a range from about any of the foregoing amounts to about any other of the foregoing amounts.

When the photopolymerization initiator is included in an amount within the above range, excellent reliability may be secured due to sufficiently curing during exposure in a pattern-forming process, a pattern may have excellent resolution and close-contacting (adhesive) properties as well as excellent heat resistance, light resistance, and chemical resistance, and transmittance may be prevented from deterioration due to a non-reaction initiator.

The solvent is a material having compatibility with the compound, the alkali soluble resin, the photopolymerizable compound, and the photopolymerization initiator but not reacting therewith.

Examples of the solvent may include without limitation alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like, and combinations thereof. Additionally, high boiling point solvents such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like, and combinations thereof may be also used.

Considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol monomethylether acetate, propylene glycol propylether acetate and the like; and ketones such as cyclohexanone may be used.

The solvent is used in a balance amount, for example about 30 wt % to about 80 wt %, based on the total amount (total weight, 100 wt %) of the photosensitive resin composition. In some embodiments, the photosensitive resin composition may include the solvent in an amount of about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 wt %. Further, according to some embodiments, the amount of the solvent can be in a range from about any of the foregoing amounts to about any other of the foregoing amounts.

When the solvent is included in an amount within the above range, the photosensitive resin composition may have an appropriate viscosity resulting in improvement of coating characteristics of a color filter.

The photosensitive resin composition according to another embodiment may further include an epoxy compound in order to improve a close contacting property with a substrate.

Examples of the epoxy compound may include without limitation phenol novolac epoxy compounds, tetramethyl biphenyl epoxy compounds, bisphenol A epoxy compounds, alicyclic epoxy compounds, and the like, and combinations thereof.

The epoxy compound may be included in an amount of about 0.01 parts by weight to about 20 parts by weight, for example about 0.1 parts by weight to about 10 parts by weight, based on about 100 parts by weight of the photosensitive resin composition. When the epoxy compound is included in an amount within the above range, close contacting properties, storage capability, and the like may be improved.

The photosensitive resin composition may further include a silane coupling agent having a reactive substituent such as a carboxyl group, a methacryloyl group, an isocyanate group, an epoxy group, and the like in order to improve adherence to a substrate.

Examples of the silane coupling agent include without limitation trimethoxysilyl benzoic acid, γ-methacryl oxypropyl trimethoxysilane, vinyl triacetoxysilane, vinyl trimethoxysilane, γ-isocyanate propyl triethoxysilane, γ-glycidoxy propyl trimethoxysilane, β-(3,4-epoxycyclohexyl) ethyltrimethoxysilane, and the like. These may be used singularly or in a mixture of two or more.

The silane coupling agent may be included in an amount of about 0.01 parts by weight to about 10 parts by weight based on about 100 parts by weight of the photosensitive resin composition. When the silane coupling agent is included in an amount within the above range, close contacting properties, storage properties, and the like can be improved.

The photosensitive resin composition may further include a surfactant in order to improve coating properties and inhibit generation of spots.

Examples of the surfactant may include without limitation fluorene-based surfactants, for example, BM-1000® and/or BM-1100® (BM Chemie Inc.); MEGAFACE F 142D®, F 172®, F 173®, and/or F 183® (Dainippon Ink Kagaku Kogyo Co., Ltd.); FULORAD FC-135®, FULORAD FC-170C®, FULORAD FC-430®, and/or FULORAD FC-431® (Sumitomo 3M Co., Ltd.); SURFLON S-112®, SURFLON S-113®, SURFLON S-131®, SURFLON S-141®, and/or SURFLON 5-145® (ASAHI Glass Co., Ltd.); SH-28PA®, SH-190®, SH-193®, SZ-6032®, and/or SF-8428®, and the like (Toray Silicone Co., Ltd.).

The surfactant may be included in an amount of about 0.001 to about 5 parts by weight based on about 100 parts by weight of the photosensitive resin composition. When the surfactant is included in an amount within the above range, coating uniformity may be ensured, stains may not be generated, and wetting properties for a glass substrate can be improved.

The photosensitive resin composition may further one or more other additives. Examples of the other additives may include without limitation antioxidants, stabilizers, and the like and combinations thereof. The additives may be present in an amount selected to provide the desired properties.

According to another embodiment of the present invention, a color filter manufactured using the photosensitive resin composition is provided.

An exemplary pattern-forming process for the color filter is as follows.

The process can include coating the positive photosensitive resin composition on a support substrate using a method such as spin coating, slit coating, inkjet printing, and the like; drying the coated positive photosensitive resin composition to form a photosensitive resin composition film; exposing the positive photosensitive resin composition film to light; developing the exposed positive photosensitive resin composition film in an alkali aqueous solution to obtain a photosensitive resin film; and heat-treating the photosensitive resin film. Conditions for the patterning process are well known to the skilled artisan and will not be illustrated in detail in the specification.

Hereinafter, the present invention is illustrated in more detail with reference to examples and comparative examples. However, the following examples and comparative examples are provided for the purpose of illustration only and the present invention is not limited thereto.

Synthesis of Compound

Synthesis Example 1

Synthesis of 3,5,6-trichloro-4-(2,4-di-tert-butylphenoxy)-phthalonitrile 3,4,5,6-tetrachlorophthalonitrile (5 g), 2,4-di-t-butylphenol (3.8 g), $K_2CO_3$ (3.898 g), and N,N-dimethylformamide (50 ml) are put in a 100 ml flask and then agitated while heated at 70° C. When the reaction is complete, the resultant product is extracted with EA (ethyl acetate). After the extraction, the product is column-purified with EA/hexane through column chromatography to obtain a liquid, the liquid is concentrated to obtain a solid, and the solid is vacuum-dried, obtaining a compound represented by Synthesis Example 1.

Synthesis Example 2

Synthesis of 3,5,6-trichloro-4-(2,6-dimethylphenoxy)-phthalonitrile 3,4,5,6-tetrachlorophthalonitrile (5 g), 2,6-dimethylphenol (6.6 g), $K_2CO_3$ (3.898 g), and acetone (50 ml) are put in a 100 ml flask and then agitated while heated at 50° C. When the reaction is complete, the resultant product is extracted with EA (ethyl acetate). After the extraction, the product is column-purified with EA/hexane through column chromatography to obtain a liquid, the liquid is concentrated to obtain a solid, and the solid is vacuum-dried, obtaining a compound represented by Synthesis Example 2.

Synthesis Example 3

Synthesis of 3,5,6-trichloro-4-(2-tert-butylphenoxy)-phthalonitrile 3,4,5,6-tetrachlorophthalonitrile (5 g), 2-tert-butylphenol (6.64 g), $K_2CO_3$ (3.898 g), and acetone (50 ml) are put in a 100 ml flask and then agitated while heated at 50° C. When the reaction is complete, the resultant product is extracted with EA (ethyl acetate). After the extraction, the product is column-purified with EA/hexane through column chromatography to obtain a liquid, the liquid is concentrated to obtain a solid, and the solid is vacuum-dried, obtaining a compound represented by Synthesis Example 3.

Synthesis Example 4

Synthesis of 3,5,6-trichloro-4-(3-methyl-butoxy)-phthalonitrile 3,4,5,6-tetrachlorophthalonitrile (5 g), Isoamyl alcohol (5.9 g), 1,8-diazabicycloundec-7-ene (3.9 g), and tetrahydrofuran (50 ml) are put in a 100 ml flask and then agitated while heated at 50° C. When the reaction is complete, the resultant product is extracted with EA (ethyl acetate). After the extraction, the product is column-purified with EA/hexane through column chromatography to obtain a liquid, the liquid is concentrated to obtain a solid, and the solid is vacuum-dried, obtaining a compound represented by Synthesis Example 4.

Synthesis Example 5

Synthesis of 3,5,6-trichloro-4-(biphenyl-2-yloxy)-phthalonitrile 3,4,5,6-tetrachlorophthalonitrile (5 g), 2-phenylphenol (3.2 g), $K_2CO_3$ (3.898 g), and acetone (50 ml) are put in a 100 ml flask and then agitated while heated at 50° C. When the reaction is complete, the resultant product is extracted with EA (ethyl acetate). After the extraction, the product is column-purified with EA/hexane through column chromatography to obtain a liquid, the liquid is concentrated to obtain a solid, and the solid is vacuum-dried, obtaining a compound represented by Synthesis Example 5.

Synthesis Example 6

Synthesis of Compound Represented by Chemical Formula 4

The compound (1 g) according to Synthesis Example 1, the compound (0.269 g) according to Synthesis Example 2, 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated, while continuously heated up to 140° C. When the reaction is complete, precipitate therein is filtered with MeOH and vacuum-dried. The dried solid is purified through column chromatography. Then, dichloromethane in a small amount is added thereto to dissolve the solid, and methanol is added thereto to perform crystallization. Herein, a solid therefrom is filtered and vacuum-dried, obtaining a compound represented by Chemical Formula 4.

[Chemical Formula 4]

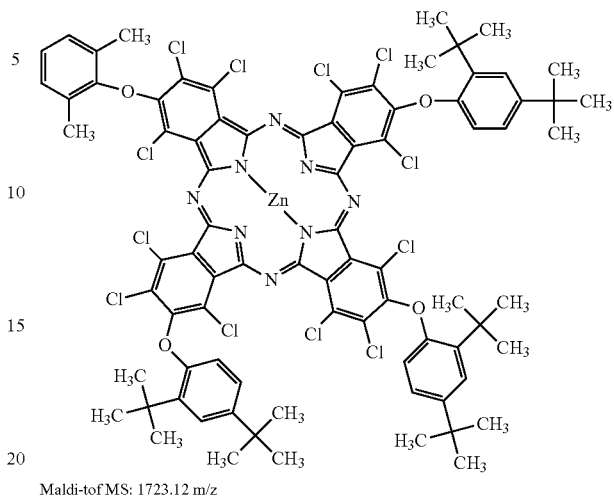

Maldi-tof MS: 1723.12 m/z

Synthesis Example 7

Synthesis of Compound Represented by Chemical Formula 5

The compound (1 g) according to Synthesis Example 1, the compound (0.288 g) according to Synthesis Example 3, 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated while continuously heated up to 140° C. When the reaction is complete, a precipitate therein is filtered with MeOH and then vacuum-dried. The dried solid is purified through column chromatography. Then, dichloromethane in a small amount is added thereto to dissolve the solid, and methanol is added thereto for crystallization. Herein, a solid obtained therefrom is filtered and vacuum-dried, obtaining a compound represented by Chemical Formula 5.

[Chemical Formula 5]

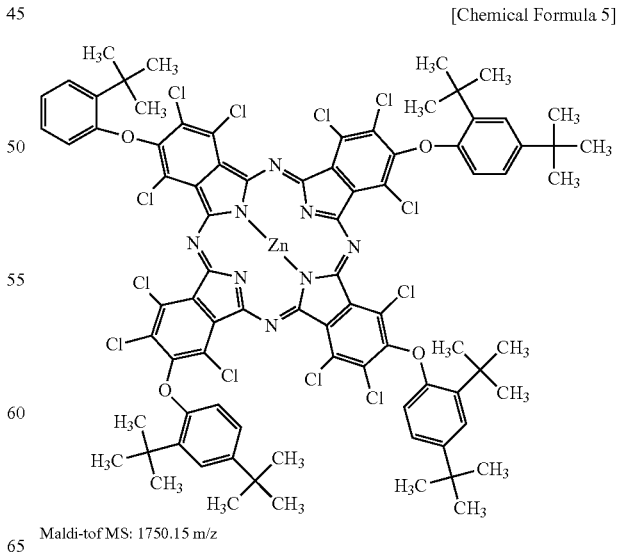

Maldi-tof MS: 1750.15 m/z

Synthesis Example 8

Synthesis of Compound Represented by Chemical Formula 6

The compound (1 g) according to Synthesis Example 1, the compound (0.24 g) according to Synthesis Example 4, 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, a solid obtained therefrom is filtered and vacuum-dried, obtaining a compound represented by Chemical Formula 6.

[Chemical Formula 6]

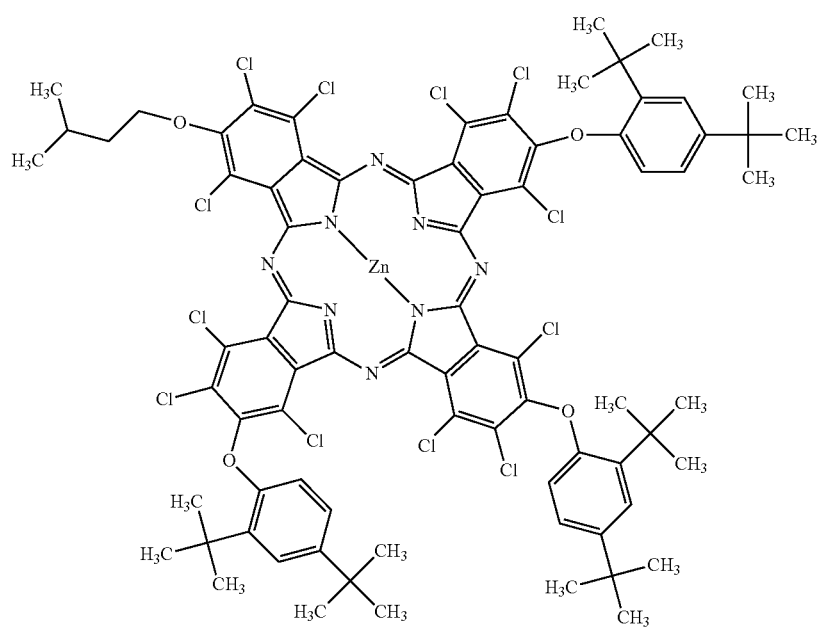

Maldi-tof MS: 1692.13 m/z

Synthesis Example 9

Synthesis of Compound Represented by Chemical Formula 7

The compound (1 g) according to Synthesis Example 1, the compound (0.30 g) according to Synthesis Example 5, 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated, while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, a solid obtained therefrom is filtered and vacuum-dried, obtaining a compound represented by Chemical Formula 7.

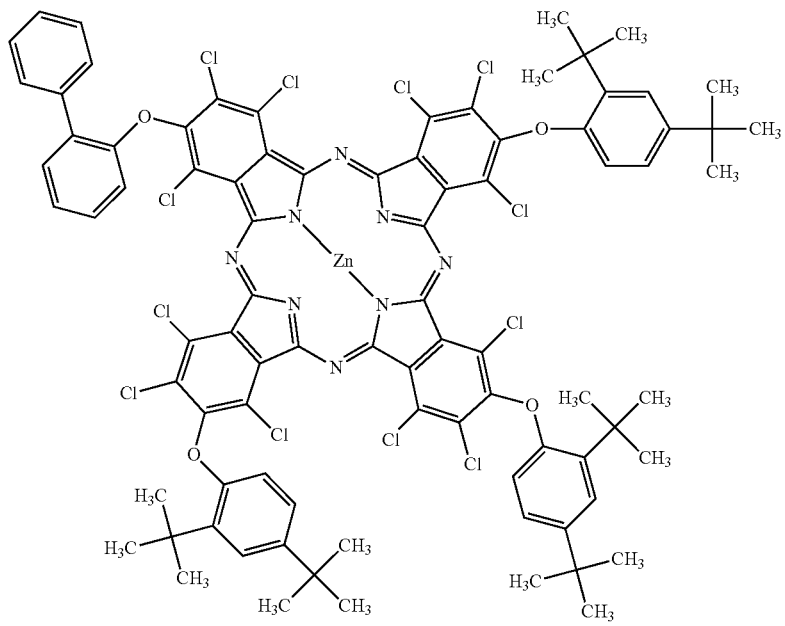

Maldi-tof MS: 1773.12 m/z

Synthesis Example 10
Synthesis of Compound Represented by Chemical Formula 8

The compound (1.45 g) according to Synthesis Example 1, 1,8-diazabicycloundec-7-ene (0.38 g), and 1-pentenol (7 g) are put in a 100 ml flask and heated at 90° C. until the solids are dissolved, zinc acetate (0.15 g) is added thereto, and the mixture is agitated while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, methanol is added thereto, and the mixture is added thereto for crystallization. Herein, the obtained solid is filtered and vacuum-dried, obtaining a compound represented by Chemical Formula 8.

[Chemical Formula 8]

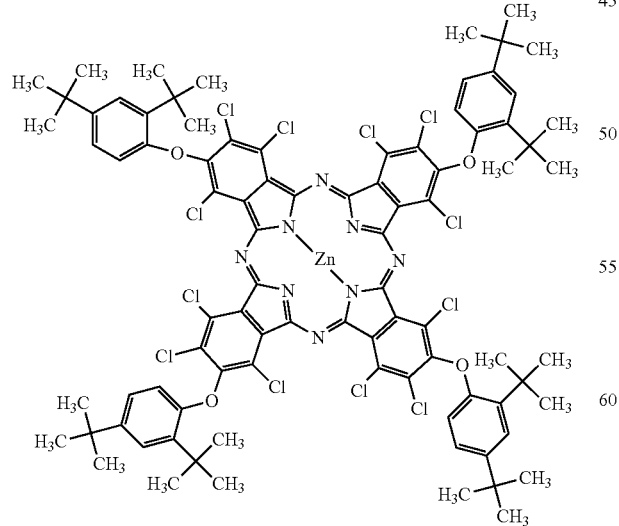

Maldi-tof MS: 1810.99 m/z

Synthesis Example 11
Synthesis of Compound Represented by Chemical Formula 9

The compound (1 g) according to Synthesis Example 1, 3,4,5,6-tetrachlorophthalonitrile (0.2 g), 1,8-diazabicycloundec-7-ene (0.6 g), and 1-pentenol (5 g) are put in a 100 ml flask and then heated at 90° C. until the solids are dissolved, zinc acetate (0.15 g) is added thereto, and the mixture is agitated, while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, the obtained solid is filtered and vacuum-dried, obtaining a compound represented by Chemical Formula 9.

[Chemical Formula 9]

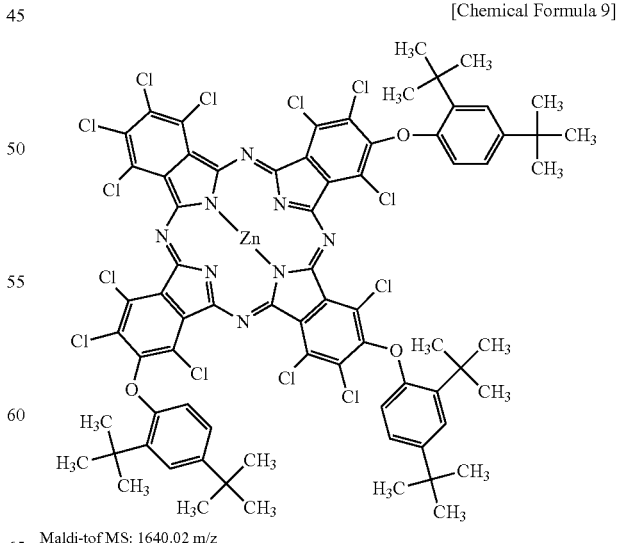

Maldi-tof MS: 1640.02 m/z

Synthesis Example 12

Synthesis of Compound Represented by Chemical Formula 10

The compound (0.40 g) according to Synthesis Example 1, 3,4,5,6-tetrachlorophthalonitrile (0.40 g), 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, a solid obtained therefrom is filtered and vacuum-dried, obtaining a compound represented by Chemical Formula 10.

[Chemical Formula 10]

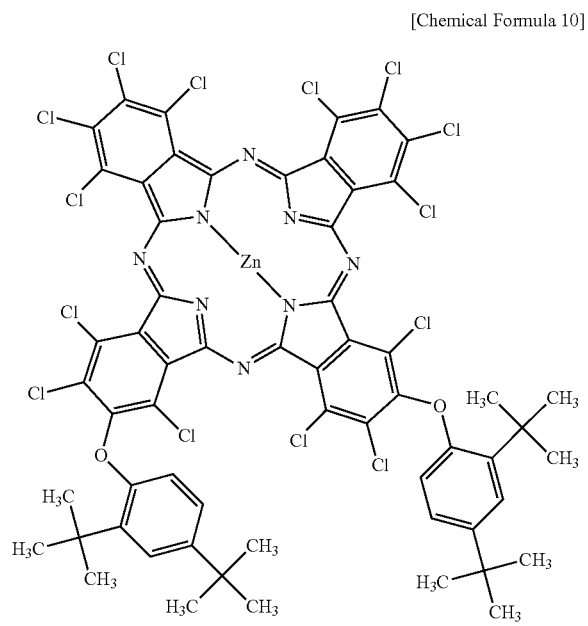

Maldi-tof MS: 1468.83 m/z

Synthesis Example 13

Synthesis of Compound Represented by Chemical Formula 11

The compound (0.33 g) according to Synthesis Example 1, 3,4,5,6-tetrachlorophthalonitrile (0.66 g), 1,8-diazabicycloundec-7-ene (0.6 g), and 1-pentenol (5 g) are put in a 100 ml flask and heated at 90° C. until the solids are dissolved, zinc acetate (0.15 g) is added thereto, and the mixture is agitated, while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, the obtained solid is filtered and vacuum-dried, obtaining a compound represented by Chemical Formula 11.

[Chemical Formula 11]

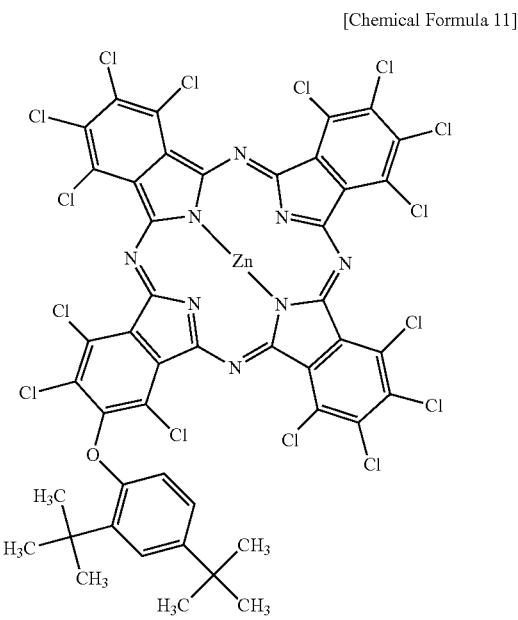

Maldi-tof MS: 1300.63 m/z

Comparative Synthesis Example 1

Synthesis of Compound Represented by Chemical Formula 12

3,5,6-trichloro-4-(phenoxy)phthalonitrile (1.0 g), 1,8-diazabicycloundec-7-ene (0.7 g), and 1-pentenol (15 mL) are put in a 100 mL flask and heated at 90° C. until the solids are dissolved, zinc acetate (0.15 g) is added thereto, and the mixture is agitated, while continuously heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, the obtained solid is filtered and vacuum-dried, obtaining a compound represented by Chemical Formula 12.

[Chemical Formula 12]

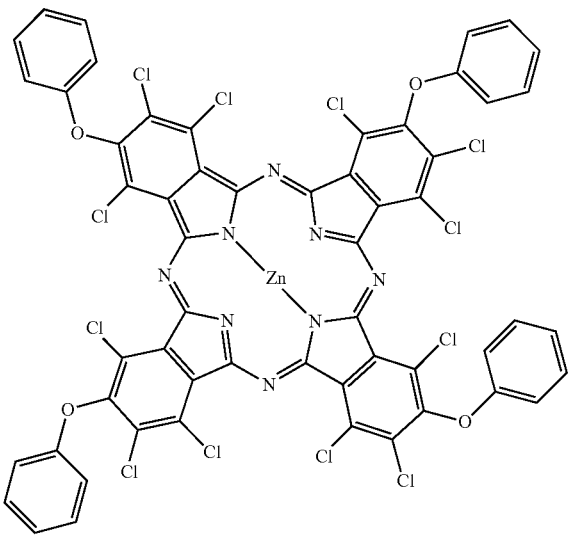

Maldi-tof MS: 1355.71 m/z

Comparative Synthesis Example 2

Synthesis of Compound Represented by Chemical Formula 13

3,5,6-trichloro-4-(pentyloxy)phthalonitrile (1 g), 1,8-diazabicycloundec-7-ene (0.7 g), and 1-pentenol (15 mL) are put in a 100 mL flask and heated at 90° C. until the solids are dissolved, zinc acetate (0.15 g) is added thereto, and the mixture is agitated until heated up to 140° C. When the reaction is complete, a precipitate therein is filtered with MeOH and vacuum-dried. The dried solid is purified through column chromatography. Then, dichloromethane in a small amount is added thereto to dissolve the solid, and methanol is added thereto for crystallization. Herein, the obtained solid is filtered and vacuum-dried, obtaining a compound represented by Chemical Formula 13.

[Chemical Formula 13]

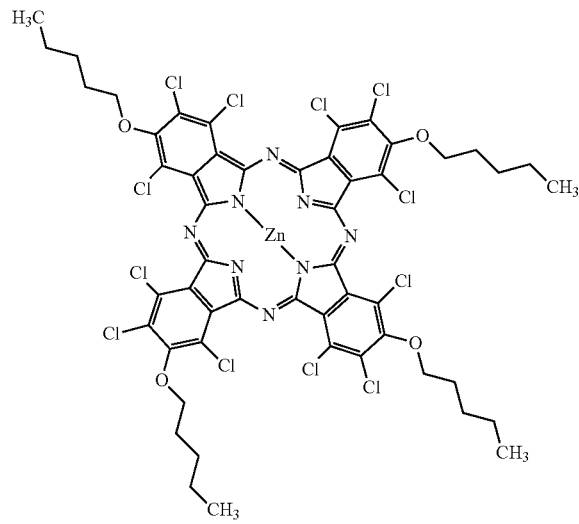

Maldi-tof MS: 1333.90 m/z

Evaluation 1: Solubility

A dilution solvent (PGMEA) is respectively added to 0.5 g of each compound according to Synthesis Examples 6 to 13 and Comparative Synthesis Examples 1 and 2, and each solution is agitated with a mixrotor (Mixrotor VMR-5, Iuchi Seieido Co., Ltd.) at 25° C. and 100 rpm for 1 hour, and solubility result of each compound is provided in Table 1.

Solubility Evaluation Reference

Dissolution of a compound (a solute) in an amount of greater than or equal to 10 wt % based on the total weight of the dilution solvent: ○

Dissolution of a compound (a solute) in an amount ranging from greater than or equal 5 wt % and less than 10 wt % based on the total weight of the dilution solvent: Δ

Dissolution of a compound (a solute) in an amount ranging from less than 5 wt % based on the total weight of the dilution solvent: X

TABLE 1

| | Solubility (unit: wt%) |
|---|---|
| Synthesis Example 6 | ○ |
| Synthesis Example 7 | ○ |
| Synthesis Example 8 | ○ |
| Synthesis Example 9 | ○ |
| Synthesis Example 10 | ○ |
| Synthesis Example 11 | ○ |
| Synthesis Example 12 | ○ |
| Synthesis Example 13 | ○ |
| Comparative Synthesis Example 1 | Δ |
| Comparative Synthesis Example 2 | Δ |

Referring to Table 1, the compounds according to Synthesis Examples 6 to 13 as a compound according to one embodiment show improved solubility in an organic solvent compared to the compounds according to Comparative Synthesis Examples 1 and 2 and thus the compounds of Synthesis Examples 6 to 13 can provide excellent color characteristics when used for a photosensitive resin composition and the like.

Synthesis of Photosensitive Resin Composition

Example 1

A photosensitive resin composition according to Example 1 is prepared by mixing the following components in a composition provided in Table 2.

A photopolymerization initiator is dissolved in a solvent, the solution is agitated at room temperature for 2 hours, an alkali soluble resin and a photopolymerizable compound are added thereto, and the mixture is agitated at room temperature for 2 hours. Subsequently, the compound according to Synthesis Example 6 (represented by Chemical Formula 4) as a colorant and a pigment (in a pigment dispersion form) are added to the reactants, and the resultant mixture is agitated at room temperature for one hour. Then, a product therefrom is three times filtered to remove impurities, preparing a photosensitive resin composition.

TABLE 2

| Material | | | Amount (unit: wt%) |
|---|---|---|---|
| Colorant | Dye | Compound of Synthesis Example 6 | 5.0 |
| | Pigment dispersion | Pigment Y138 pigment dispersion | 15.0 |
| Alkali soluble resin | | (A)/(B) = 15/85 (w/w), molecular weight (Mw) = 22,000 g/mol (A): methacrylic acid (B): benzylmethacrylate | 3.5 |
| Photopolymerizable compound | | dipentaerythritolhexaacrylate (DPHA) | 8.0 |
| Photopolymerization initiator | | 1,2-octandione | 1.0 |
| | | 2-dimethylamino-2-(4-methyl-benzyl)-1-(4-morpholin-4-yl-phenyl)-butan-1-one | 0.5 |
| Solvent | | cyclohexanone | 37.0 |
| | | PGMEA (propylene glycol mono-methyl ether acetate) | 30.0 |
| | | Total | 100.00 |

Example 2

A photosensitive resin composition is prepared according to the same method as Example 1 except for using the compound of Synthesis Example 7 (represented by Chemical Formula 5) instead of the compound of Synthesis Example 6 (represented by Chemical Formula 4).

Example 3

A photosensitive resin composition is prepared according to the same method as Example 1 except for using the compound of Synthesis Example 8 (represented by Chemical Formula 6) instead of the compound of Synthesis Example 6 (represented by Chemical Formula 4).

Example 4

A photosensitive resin composition is prepared according to the same method as Example 1 except for using the compound of Synthesis Example 9 (represented by Chemical Formula 7) instead of the compound of Synthesis Example 6 (represented by Chemical Formula 4).

Example 5

A photosensitive resin composition is prepared according to the same method as Example 1 except for using the compound of Synthesis Example 10 (represented by Chemical Formula 8) instead of the compound of Synthesis Example 6 (represented by Chemical Formula 4).

Example 6

A photosensitive resin composition is prepared according to the same method as Example 1 except for using the compound of Synthesis Example 11 (represented by Chemical Formula 9) instead of the compound of Synthesis Example 6 (represented by Chemical Formula 4).

Example 7

A photosensitive resin composition is prepared according to the same method as Example 1 except for using the compound of Synthesis Example 12 (represented by Chemical Formula 10) instead of the compound of Synthesis Example 6 (represented by Chemical Formula 4).

Example 8

A photosensitive resin composition is prepared according to the same method as Example 1 except for using the compound of Synthesis Example 13 (represented by Chemical Formula 11) instead of the compound of Synthesis Example 6 (represented by Chemical Formula 4).

Comparative Example 1

A photosensitive resin composition is prepared according to the same method as Example 1 except for using the compound of Comparative Synthesis Example 1 (represented by Chemical Formula 12) instead of the compound of Synthesis Example 6 (represented by Chemical Formula 4).

Comparative Example 2

A photosensitive resin composition is prepared according to the same method as Example 1 except for using the compound of Comparative Synthesis Example 2 (represented by Chemical Formula 13) instead of the compound of Synthesis Example 6 (represented by Chemical Formula 4).

Comparative Example 3

A photosensitive resin composition is prepared according to the same method as Example 1 except for using the composition provided in Table 3 instead of the composition provided in Table 2.

TABLE 3

| Material | | | Amount (unit: wt%) |
|---|---|---|---|
| Colorant | Pigment dispersion | Pigment G58 pigment dispersion | 20.0 |
| | | Pigment Y138 pigment dispersion | 15.0 |
| Alkali soluble resin | | (A)/(B) = 15/85 (w/w), molecular weight (Mw) = 22,000 g/mol (A): methacrylic acid (B): benzylmethacrylate | 2.5 |
| Photopolymerizable compound | | Dipentaerythritolhexaacrylate (DPHA) | 5.0 |
| Photopolymerization initiator | | 1,2-octandione | 1.0 |
| | | 2-dimethylamino-2-(4-methyl-benzyl)-1-(4-morpholin-4-yl-phenyl)-butan-1-one | 0.5 |

TABLE 3-continued

| Material | | (unit: wt%) Amount |
|---|---|---|
| Solvent | cyclohexanone | 40.0 |
| | PGMEA (propylene glycol monomethyl ether acetate) | 16.0 |
| | Total | 100.00 |

Evaluation 2: Color Coordinate, Luminance, and Contrast Ratio

Each photosensitive resin composition according to Examples 1 to 8 and Comparative Examples 1 to 3 are coated to be 1 μm to 3 μm thick on a 1 mm-thick degreased and washed glass substrate and dried on a 90° C. hot plate for 2 minutes, obtaining a film. The film is exposed by using a high pressure mercury lamp having a main wavelength of 365 nm. Then, the film is dried in a 200° C. forced convection drying furnace for 5 minutes. The color coordinate (x, y), luminance Y, and contrast ratio of the pixel layer are measured by using a spectrophotometer (MCPD3000, Otsuka Electronics Inc.) and provided in Table 4.

TABLE 4

| | Color coordinate (x, y) | Luminance Y | Contrast ratio |
|---|---|---|---|
| Example 1 | 0.272, 0.578 | 62.9 | 15,800 |
| Example 2 | 0.273, 0.579 | 62.7 | 15,700 |
| Example 3 | 0.275, 0.576 | 62.3 | 15,500 |
| Example 4 | 0.277, 0.581 | 62.5 | 15,600 |
| Example 5 | 0.278, 0.576 | 62.5 | 15,400 |
| Example 6 | 0.271, 0.579 | 62.3 | 15,300 |
| Example 7 | 0.271, 0.579 | 62.2 | 15,200 |
| Example 8 | 0.273, 0.577 | 61.9 | 15,300 |
| Comparative Example 1 | 0.277, 0.578 | 60.5 | 14,900 |
| Comparative Example 2 | 0.276, 0.580 | 59.1 | 14,100 |
| Comparative Example 3 | 0.271, 0.579 | 59.0 | 13,300 |

Referring to Table 4, the photosensitive resin compositions including a compound according to one embodiment as a dye according to Examples 1 to 8 show excellent color characteristics compared with the photosensitive resin compositions according to Comparative Examples 1 to 3.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A compound represented by Chemical Formula 1:

[Chemical Formula 1]

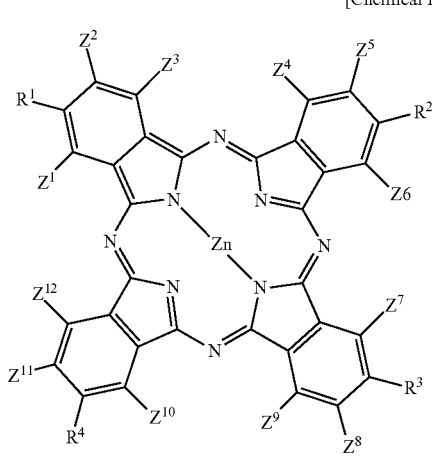

wherein, in Chemical Formula 1,
M is Cu, Zn, Co, Al, Ga, In, Ca, Mo, or Mg,
$Z^1$ to $Z^{12}$ are the same or different and are each independently Cl or Br,
$R^1$ to $R^4$ are the same or different and are each independently a halogen atom, a substituted or unsubstituted C1 to C20 alkyl group, a substituted C3 to C20 alkoxy group, a substituted or unsubstituted C6 to C20 aryl group, or a substituted or unsubstituted C6 to C20 aryloxy group, with the proviso that at least one of $R^1$ to $R^4$ is represented by Chemical Formula 2,

[Chemical Formula 2]

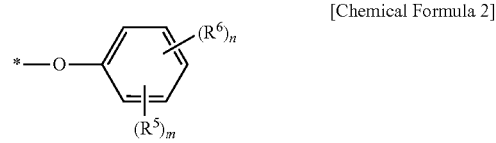

wherein in Chemical Formula 2,
$R^5$ and $R^6$ are the same or different and are each independently an unsubstituted C1 to C10 alkyl group or a C1 to C10 alkyl group-substituted C1 to C10 alkyl group, and
m and n are each independently an integer of 1.

2. The compound of claim 1, wherein $R^5$ and $R^6$ each independently comprises a t-butyl group at the terminal end.

3. The compound of claim 1, wherein Chemical Formula 2 is represented by Chemical Formula 3:

[Chemical Formula 3]

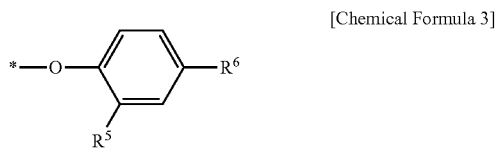

wherein in Chemical Formula 3,
$R^5$ and $R^6$ are the same or different and are each independently an unsubstituted C1 to C10 alkyl group or a C1 to C10 alkyl group-substituted C1 to C10 alkyl group.

4. The compound of claim 1, wherein at least two of $R^1$ to $R^4$ are represented by Chemical Formula 2.

5. The compound of claim 1, wherein at least three of $R^1$ to $R^4$ are represented by Chemical Formula 2.

6. The compound of claim 1, wherein all of $R^1$ to $R^4$ are represented by Chemical Formula 2.

7. The compound of claim 1, wherein the compound represented by Chemical Formula 1 is represented by one or more of Chemical Formula 4 to Chemical Formula 11:
[Chemical Formula 4]
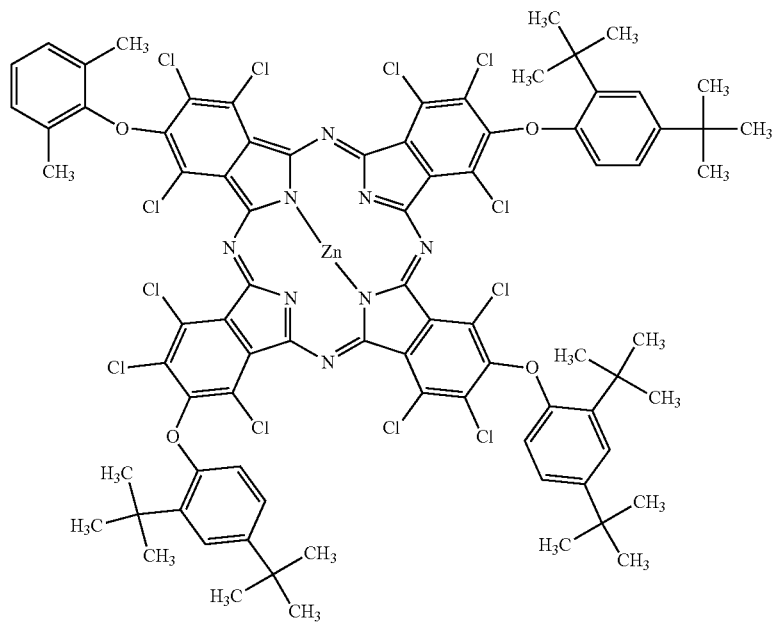
[Chemical Formula 5]
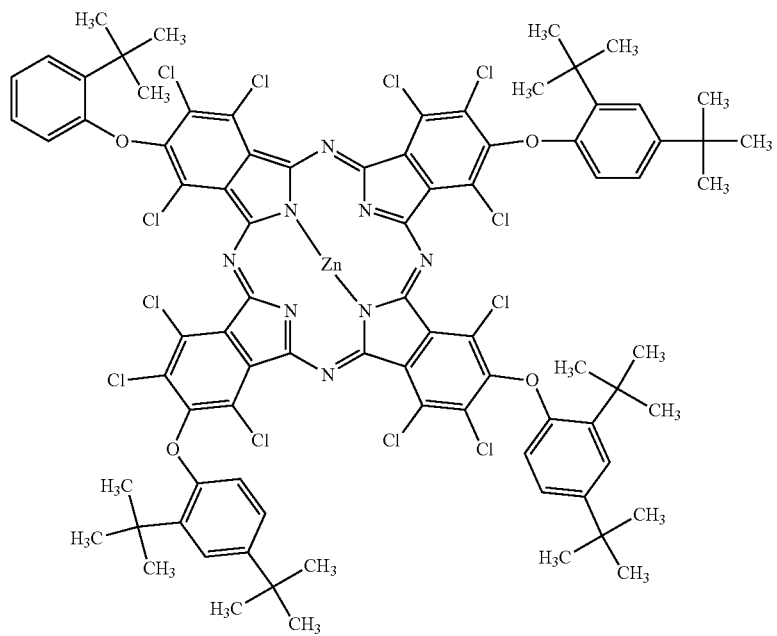

-continued
[Chemical Formula 6]
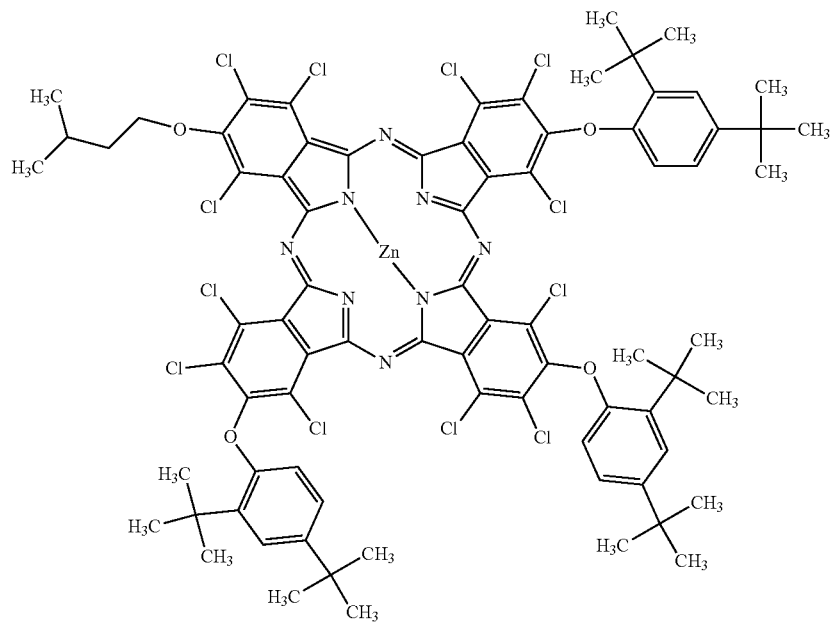
[Chemical Formula 7]
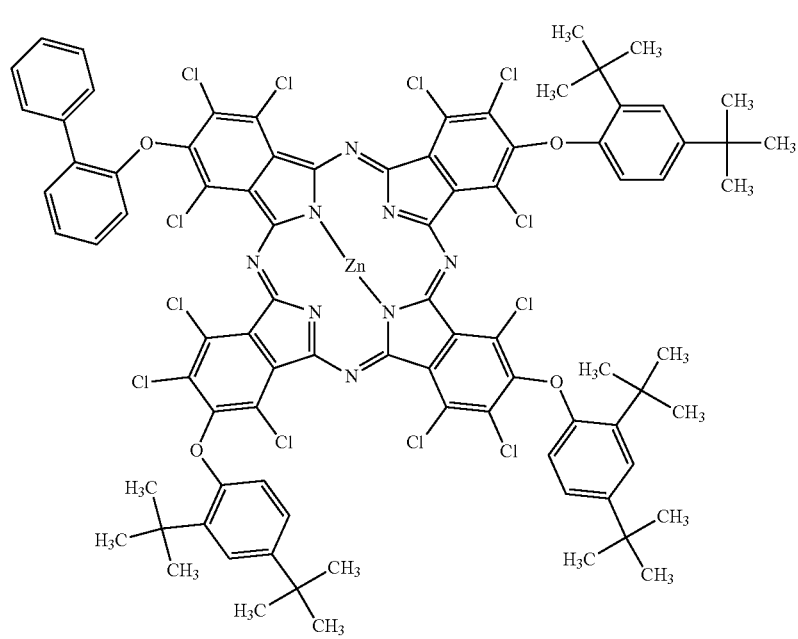

-continued
[Chemical Formula 8]
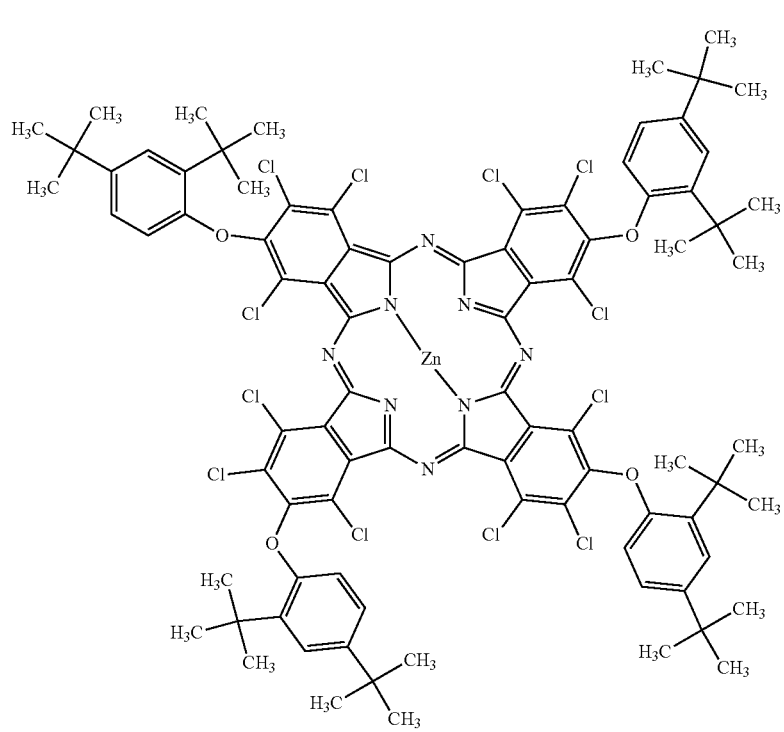
[Chemical Formula 9]
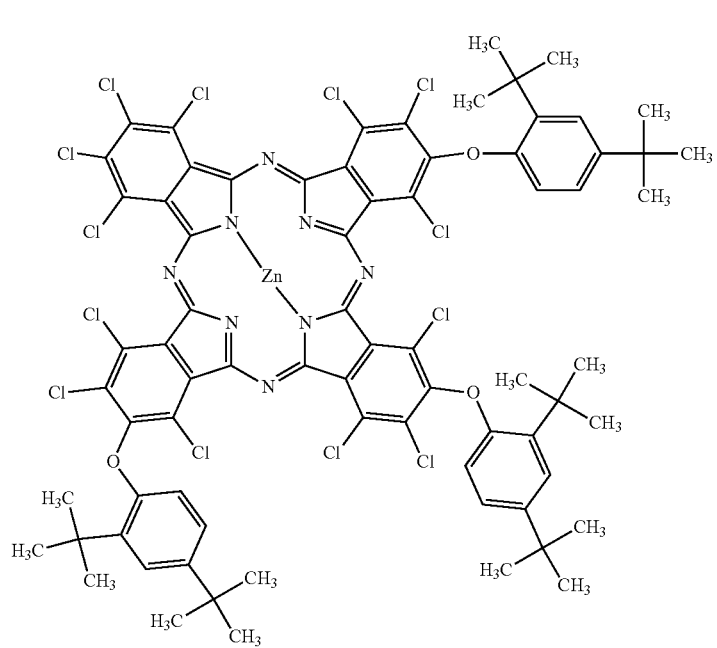

[Chemical Formula 10]

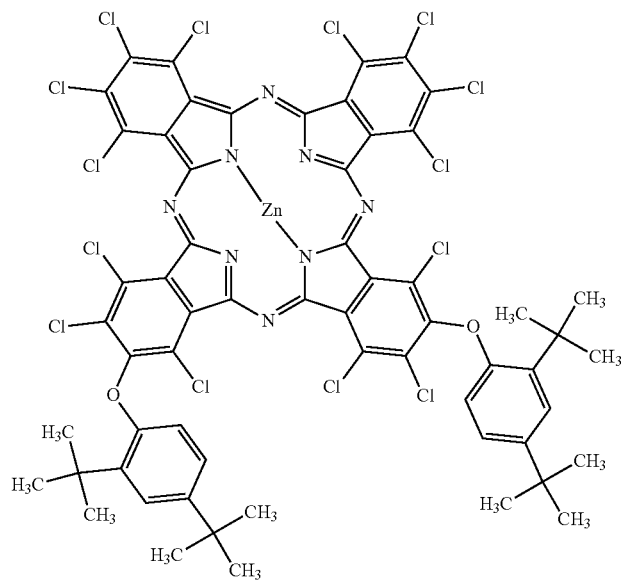

[Chemical Formula 11]

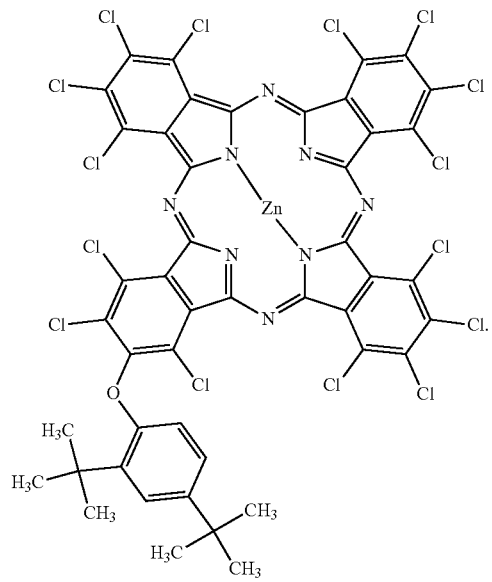

8. The compound of claim 1, wherein the compound is a green dye.

9. The compound of claim 8, wherein the green dye has a maximum transmittance in a wavelength of about 445 nm to about 560 nm.

10. A photosensitive resin composition comprising the compound of claim 1.

11. The photosensitive resin composition of claim 10, wherein the photosensitive resin composition further comprises an alkali soluble resin, a photopolymerizable compound, a photopolymerization initiator, and a solvent.

12. The photosensitive resin composition of claim 11, wherein the photosensitive resin composition further comprises a pigment.

13. The photosensitive resin composition of claim 12, wherein the pigment is a yellow pigment.

14. A color filter manufactured using the photosensitive resin composition of claim 10.

* * * * *